United States Patent
Schmotzer et al.

[11] Patent Number: 5,954,770
[45] Date of Patent: Sep. 21, 1999

[54] ENDOPROSTHETIC KNEE JOINT

[75] Inventors: Hans Schmotzer, Aarau; Willi Horber, Zurich, both of Switzerland

[73] Assignee: Plus Endoprothetik AG, Rotkrenz, Switzerland

[21] Appl. No.: 08/803,989

[22] Filed: Feb. 21, 1997

[30] Foreign Application Priority Data

Feb. 21, 1996 [DE] Germany .............................. 196 06 462

[51] Int. Cl.⁶ ....................................................... A61F 2/38
[52] U.S. Cl. ............................................................... 623/20
[58] Field of Search ...................................... 623/16, 18, 20

[56] References Cited

U.S. PATENT DOCUMENTS

| | | | |
|---|---|---|---|
| 3,868,730 | 3/1975 | Kaufer et al. .............................. | 623/20 |
| 3,996,624 | 12/1976 | Noiles ....................................... | 623/20 |
| 4,112,522 | 9/1978 | Dadurian et al. ........................ | 623/204 |
| 4,136,405 | 1/1979 | Pastrick et al. . | |
| 4,219,893 | 9/1980 | Noiles ....................................... | 623/20 |
| 4,301,553 | 11/1981 | Noiles . | |
| 4,462,120 | 7/1984 | Rambert et al. . | |
| 4,538,306 | 9/1985 | Dorre et al. .............................. | 623/20 |
| 4,662,889 | 5/1987 | Zichner et al. ........................... | 623/20 |
| 5,139,521 | 8/1992 | Schelhas . | |
| 5,282,867 | 2/1994 | Mikhail ..................................... | 623/20 |
| 5,370,701 | 12/1994 | Finn .......................................... | 623/20 |
| 5,411,555 | 5/1995 | Nieder ...................................... | 623/20 |
| 5,413,607 | 5/1995 | Engelbrecht et al. .................... | 623/20 |
| 5,458,644 | 10/1995 | Grundei .................................... | 623/20 |
| 5,489,311 | 2/1996 | Cipolletti . | |

FOREIGN PATENT DOCUMENTS

| | | |
|---|---|---|
| 174531 | 3/1986 | European Pat. Off. . |
| 639358 | 2/1995 | European Pat. Off. . |
| 3529894 | 3/1987 | Germany . |
| 4102509 | 7/1992 | Germany . |
| 2088724 | 6/1982 | United Kingdom . |

*Primary Examiner*—Mary Beth Jones
*Attorney, Agent, or Firm*—Knobbe, Martens, Olson & Bear, LLP

[57] ABSTRACT

An endoprosthetic knee joint has a femur portion, a tibia portion, and a coupling portion. The femur portion has a femur shaft having convexly curved condyle shells at a lower end, the shells having primary slide surfaces and two spaced apart side walls forming an intercondylar space. The tibia portion has a tibia shaft with a tibia plateau at an upper end, upon which are formed secondary slide surfaces. The tibia plateau has an axial recess. The coupling portion has a coupling pin rotatably housed in the recess, and a joint head at the upper end of the pin projects into the intercondylar space. The joint head has a bore extending transversely to the femur axis and is pivotally mounted by a coupling bolt which extends through the bore and is supported on the side walls of the condyle shells. A slide bush may be provided about the medial portion of the coupling bolt to enhance flexion/extension capability and varus/valgus movement. This knee joint provides higher resistance to breakage and enables varus/valgus compensation in the case of erroneous axial positionings.

18 Claims, 10 Drawing Sheets

ENDOPROSTHETIC KNEE JOINT

BACKGROUND OF THE INVENTION

The invention relates to an endoprosthetic knee joint with a femur portion having, at the lower end of a femur shaft, convexly curved condylar shells with first sliding surfaces which have dorsally two spaced-apart side walls forming an intercondylar space, with a tibia portion having at the upper end of a tibia shaft a tibia plateau upon which there are formed secondary sliding surfaces corresponding to the first sliding surfaces of the condylar shells, and which has an aperture extending axially in the tibia shaft, and with a coupling portion having, at the upper end of a coupling pin accommodated rotatably in the aperture, a joint head projecting into the intercondylar space, said joint head having a bore extending transversely to the femur axis, and being pivotally mounted by means of a coupling bolt passing through the bore and supported on the adjacent side walls of the condylar shells.

Such an endoprosthetic knee joint with a coupling portion in the form of a pure hinge joint is known from DE 35 29 894 C2. The disadvantage of such an endoprosthetic knee joint resides particularly in the fact that, when there are axial faulty positionings between the femur and the tibia, no varus/valgus compensation is possible and the resultant one-sided load must be taken up totally by the coupling bolt or its anchorage in the side walls. As it is in many cases conventional for reasons of weight-saving to connect the two side walls of the condylar shells by means of a web to form a box, upon which the femur shaft is then set, box breakages with a lack of possibility for varus/valgus compensation are well-known consequences. This problem was recognised at an early stage, and the rigid coupling bolt was replaced by a sphere which is attached to the point of a stem emerging from the tibia portion and accommodated in a corresponding bowl in the box of the femur portion after the fashion of a joint head. Such an endoprosthetic knee joint is known from EP 0 639 358 or from GB-A-2,088,724. The problem in such a spherical construction resides in suspending the sphere in the bowl and in the latent risk of dislocation in the case of traction or extreme movement. The risk of dislocation is intended to be partly counteracted by the fact that the stem upon whose point the sphere is attached was not rigidly connected to the tibia portion, but was let into a recess in the tibia shaft, whereupon in the case of tension stress, the ball joint was not drawn out of the bowl, but the stem out of the recess, which is of little importance due to the long distance covered.

There is known from DE-OS 41 02 509 a more recent construction of an endoprosthetic knee joint with a hinge joint, in which a stationary sphere on a stem and a slotted bowl secured to the femur portion are provided. The problem of suspension and of dislocation becomes clear with reference to this known construction.

Finally, a further problem arises in all these spherical constructions, from the fact that the most important forces acting on the coupling bolt are oscillating, anteriorposterior thrust forces, which cannot be neutralised, or only to a slight degree, by the lateral hemispheres articulated to the box wall, so that the supporting surfaces on the central portions of the sphere or of the ball are reduced and consequently there is a risk of overloading.

SUMMARY OF THE INVENTION

In contrast to this, an object of the present invention is further to develop an endoprosthetic knee joint of the type already mentioned in such a way that the disadvantages described are avoided, and in particular there is a simple possibility of varus/valgus compensation.

This object is achieved in the endoprosthetic knee joint according to the present invention by four different embodiments given by way of example. In the first embodiment, the portion of the coupling bolt located inside the bore of the joint head has a spherically-formed outer peripheral surface, which co-operates with a correspondingly-shaped sliding surface of the joint head.

The advantages of this embodiment according to the invention reside particularly in the fact that the joint head surrounding the spherically-shaped axis is tilted until it stops at the side walls of the condylar shells in the varus or valgus direction, or can be rotated parallel to the tibia axis.

In the second embodiment according to the invention, the portion of the coupling bolt located within the bore of the joint head is in the shape of a cylinder, whose axis extends transversely to the longitudinal axis of the coupling bolt, the cylinder co-operating with the correspondingly-shaped sliding surface within the joint head, and in that the coupling bolt is pivotally mounted on the side walls of the condylar shells, in order to enable a flexion/extension movement. Thus the axis of the cylinder extends in the anterior/posterior direction. In this embodiment also there are the advantages of mobility of the joint head in the varus or valgus direction, while here however rotation about the tibia axis or parallel thereto is not possible. In the first and second embodiments described, the sliding surface of the joint head can comprise a material which on the one hand is slidable and on the other is resistant. This material is preferably plastic or the same material from which the coupling bolt is made (e.g., metal/metals; ceramic/ceramics, etc.) In both cases the corresponding material, insofar as it is not in any case identical with that of the joint head, may be let into the joint head in the form of a bearing bush.

The two further embodiments according to the invention utilise the principle of the two embodiments already described, yet contain a slide bush thrust on to the coupling bolt, and which sits in the bore in the joint head, and which enables both a flexion/extension movement and also a varus/valgus movement between the tibia portion and the femur portion of the endoprosthetic knee joint.

According to the third embodiment according to the invention therefore, the slide bush has a spherically-shaped external peripheral surface, which co-operates with a correspondingly-shaped sliding surface of the joint head. Here also the annular joint head surrounding the spherical slide bush can be tilted until it stops against the side walls of the condylar shells in the varus or valgus direction or can to a restricted degree be parallel to the tibia axis. In order to allow the flexion/extension movement to take place exclusively between the outer peripheral surface of the slide bush and the corresponding sliding surface of the joint head, the slide bush may be non-rotarily connected to the coupling bolt.

Finally, in the fourth embodiment according to the invention, the slide bush is in the shape of a cylinder, whose longitudinal axis extends transversely to the axis of the bore in the joint head, here also the cylindrical slide bush having a ventral-dorsal alignment and co-operating with a correspondingly-shaped sliding surface within the joint head.

The advantage in using the slide bushes resides in the fact that friction between the coupling bolt and the sliding surface of the joint head is reduced. In addition, the slide bushes enable sub-division of the joint surface into a purely cylindrical part for the flexion/extension movement between the coupling bolt and the slide bush, and into a spherical or further cylindrical part for the varus/valgus movement between slide bush and joint head. The spherical part of the joint surface also enables a restricted rotary movement between the slide bush and the joint head.

In turn, the slide bush can consist of a uniform material, preferably plastics, metal or ceramics. It can have however have another material on the slide surfaces. Thus for example it may be imagined that the convex-shaped outer surface comprises a hard material, e.g., metal or ceramics, while the concave shaped inner slide surface comprises a soft material, e.g., plastics which, according to a further development of the present invention, can be let into the slide bush in the form of a bearing bush.

The advantages of all four embodiments of the invention reside in a particularly durable stable construction of the knee joint. For in view of the fact that only the central spherical or cylindrical portion of the coupling bolt is used as a joint axis, and the coupling bolt is otherwise rigidly connected to the side walls of the condylar discs, the non-supporting lateral hemispheres known from prior art are omitted. For this reason the central spherical or cylindrical portion of the coupling bolts may be of greater dimensions more reliably accepting stress, which in all results in higher resistance to breakage and higher load capacity of the endoprosthetic knee joint according to the invention.

For the embodiments 1, 3 and 4 described above, the coupling bolt is preferably non-rotarily mounted on the adjacent side walls of the condyle shells, i.e., is rigidly connected to the side walls. The advantage of this preferred method of securing the coupling bolt resides in the fact that the risk of dislocation is to the largest extent avoided. Basically however, it is possible in all four embodiments according to the invention to mount the coupling bolt pivotally in the side walls of the condyle shells.

The parallel spacing of the side walls of the condyle shells is preferably of such dimensions that the varus/valgus mobility is restricted to a predeterminable angular range γ, which lies for example between 0° and ±10°.

In order to reduce wear between the lateral surfaces of the joint head and the side walls of the condyle shells a respective disc is located at that point, which may for example consist of polyethylene.

The lateral surfaces of the joint head are preferably formed in the radial direction on both sides in a convex-conical configuration, resulting in superficial stoppage of the side surfaces at the side walls of the condyle shells or on the interposed disc, and thus, with simultaneous flexion/extension movement, no grooves are ground in as a result of edge pressure.

In addition, by means of partly conical (roof-shaped) bevelling of the side surfaces of the joint head, rotation of the joint head can be excluded, which is superfluous as the necessary rotation can take place around the axis of the coupling pin. Finally it is also possible, by means of a corresponding conical design of the inner sides of the discs facing the joint head, to restrict the varus/valgus movement and the rotary movement.

BRIEF DESCRIPTION OF THE DRAWINGS

In the following, the four embodiments of the endoprosthetic knee joint according to the invention are described in more detail with reference to the drawings.

DETAILED DESCRIPTION OF THE PREFERRED EMBODIMENTS

Figure 1:
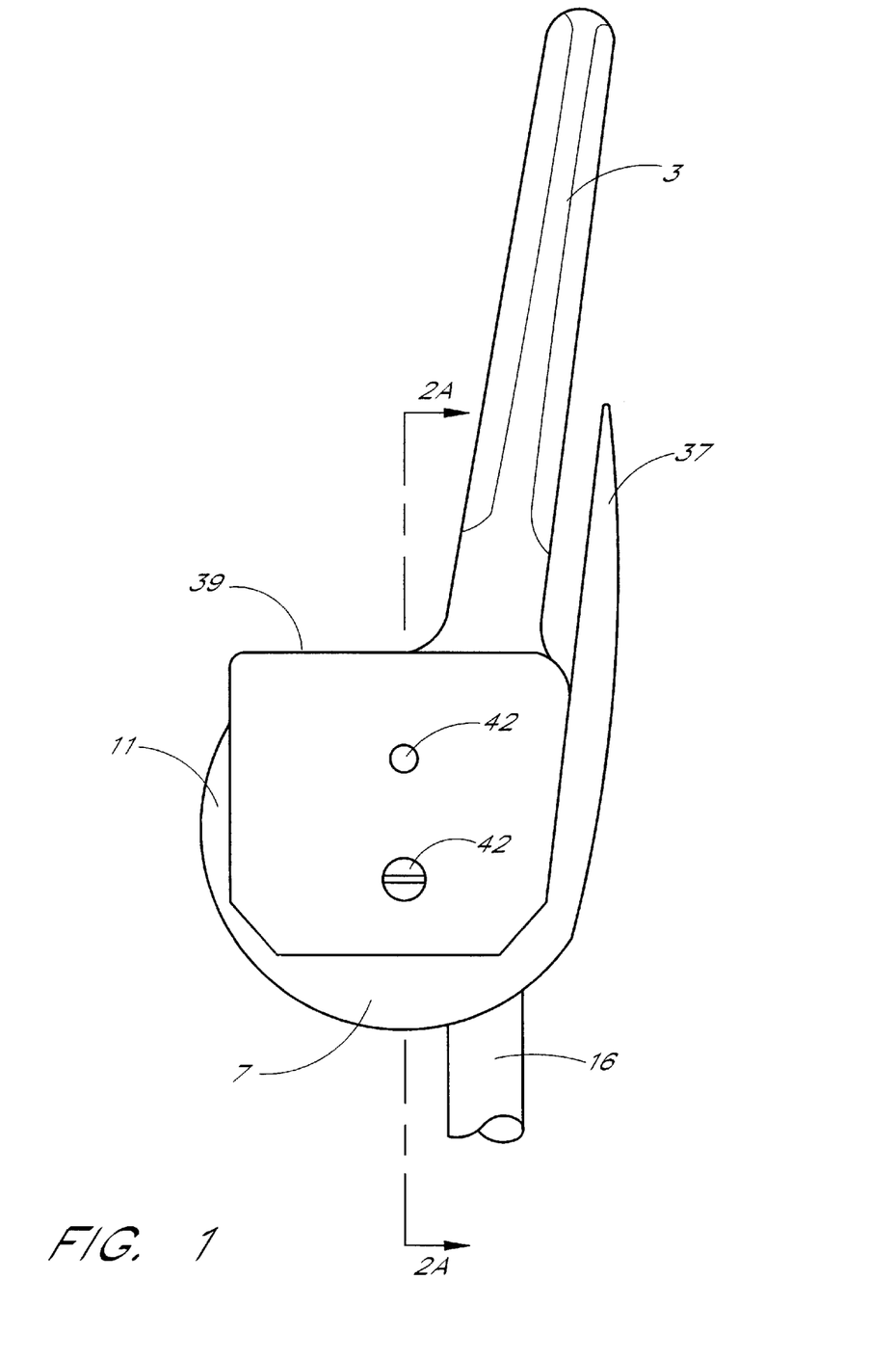
FIG. 1 is an elevation view of the endoprosthetic knee joint according to the present invention.

FIG. 1 shows an elevation view of the endoprosthetic knee joint of the present invention. FIGS. 2A, 2B, 2C, and 2D show exploded views of the four embodiments of the endoprosthetic knee joint, respectively. Each of these four embodiments substantially comprises four component groups: a femur portion 1 with a femur shaft 3 and convexly curved condyle shells 5, 7 located on its lower end, said shells 5, 7 being extensively adapted to the natural condyle and having on their underside primary slide surfaces 9, 11 and which have dorsally two spaced-apart side walls 13, 15 which are connected by a web to form a box 39, and form an inter-condylar space within the box 39. The two condyle shells 5, 7 merge ventrally into one another and at that point form a patella plate 37 for articulation with the patella.

The pendant to the femur portion 1 is a tibia portion 2 with a tibia shaft 4 and a tibia plateau 6 at its upper end, which has a support surface 36 having a recess 12 extending axially in the tibia shaft 4 and a lateral edge 33 for receiving a third component group 31.

This third component group 31 comprises an inlay with a base surface 34 for mounting on the support surface 36 of the tibia portion 2, with a sleeve member 35 resting on the base surface 34, and being thrust into the recess 12 in the tibia portion 2 in order to secure the inlay 31 on the tibia portion 2, further with secondary slide surfaces 8, 10 on the upper side 52 of the inlay 31, which are concavely curved in the ventral-dorsal direction and upon which the condyle shells 5, 7 of the femur portion 1 are supported. In order to secure the fourth component group, the coupling portion 14, to the tibia portion 2, the inlay 31 has a bore 32, which extends through the upper side 52 of the inlay and through the sleeve member 35.

The coupling portion 14 has as its central element a coupling pin 16 and at its upper end a joint head 18 projecting at its upper end into an intercondylar space of the femur portion 1. In the assembled state of the endoprosthetic knee joint, the coupling pin 16 is rotatably accommodated in the bore 32 of the inlay and thus in the recess 12 in the tibia portion 2. The joint head 18 has a bore 22 extending transversely to the tibia axis 20 or transversely to the femur axis 21.

Figure 2A:
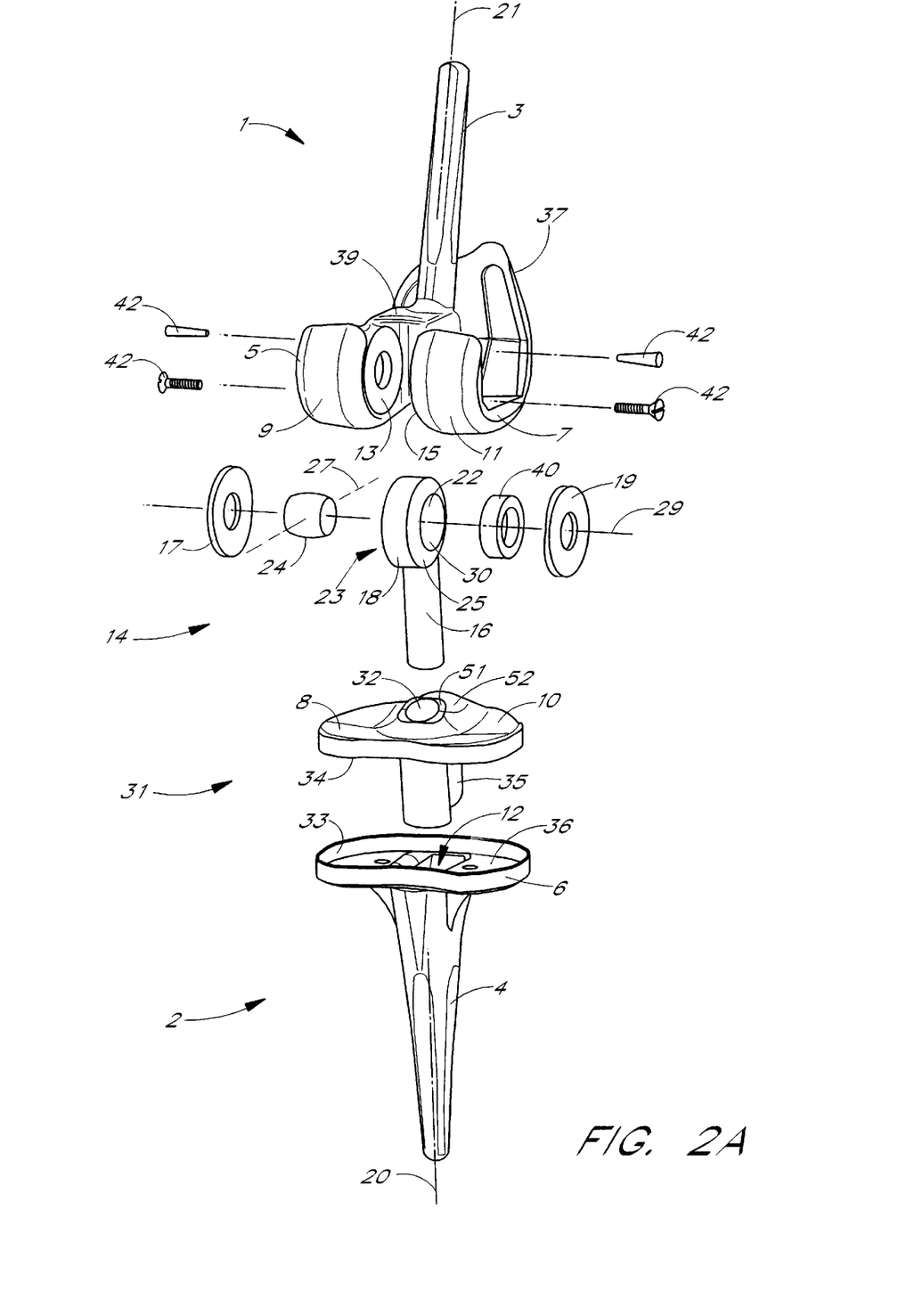
FIG. 2A is an exploded view of an endoprosthetic knee joint with a spherical coupling bolt.
Figure 2B:
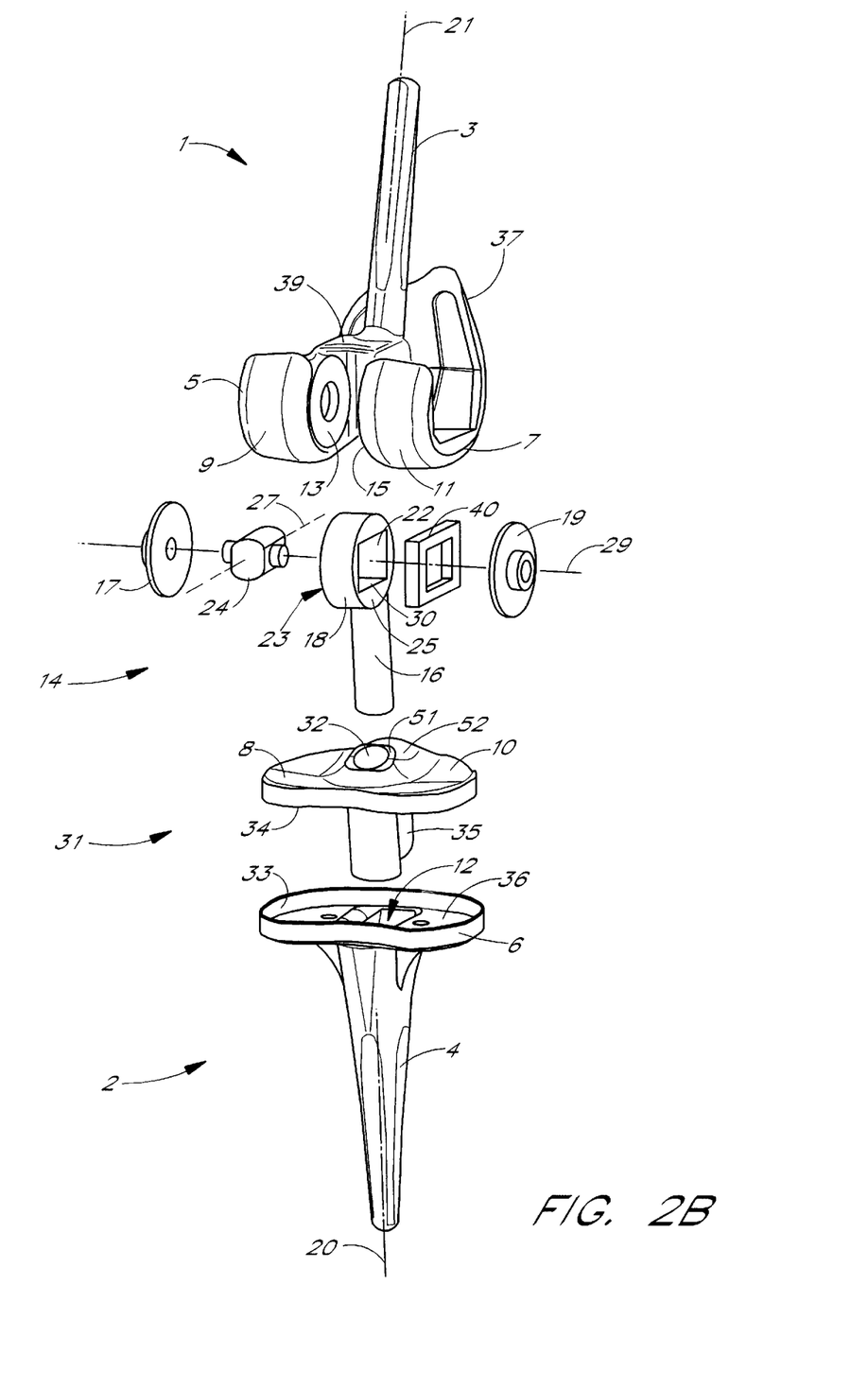
FIG. 2B is an exploded view of an endoprosthetic knee joint with a cylindrical coupling bolt.
Figure 2C:
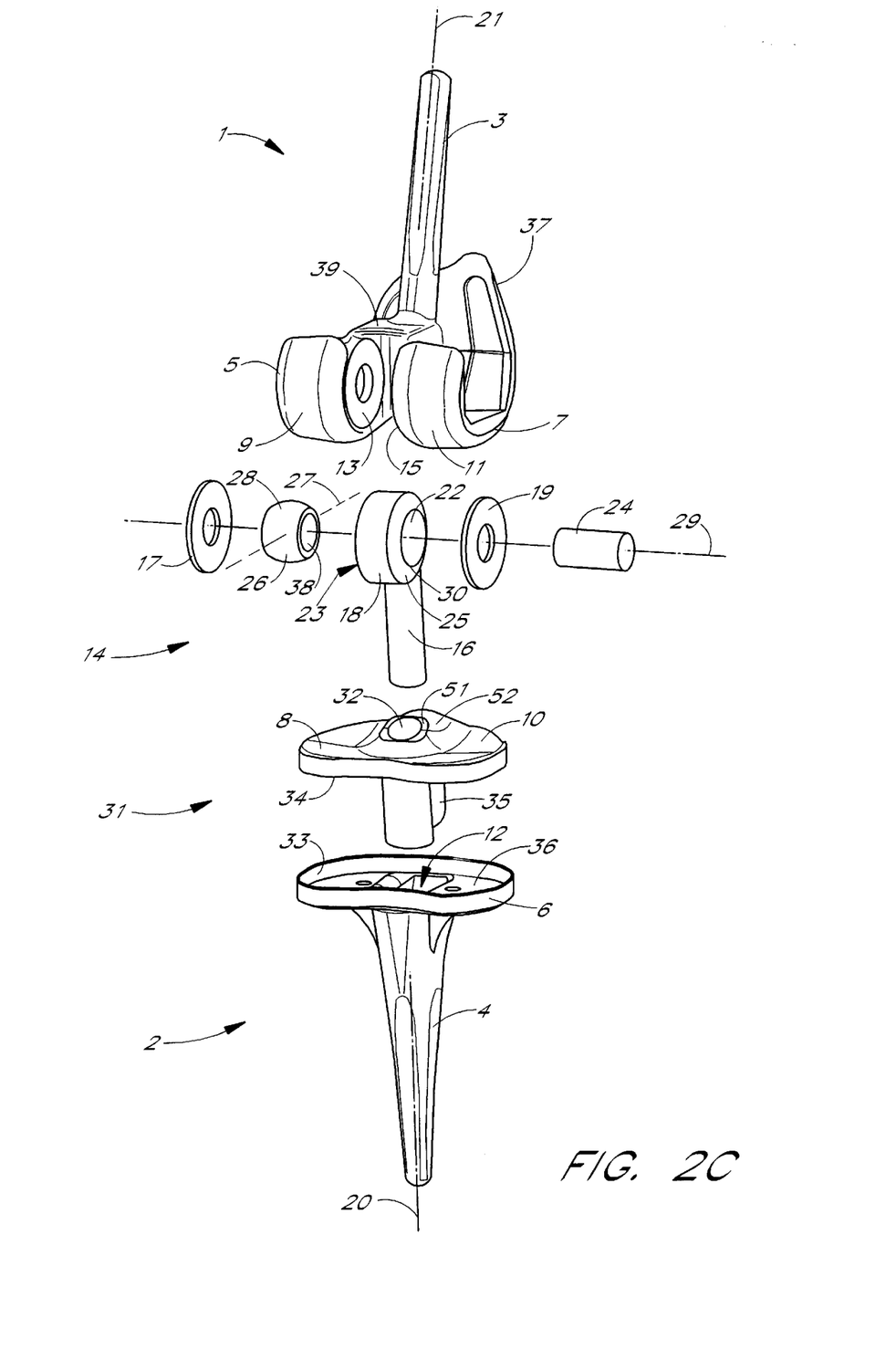
FIG. 2C is an exploded view of an endoprosthetic knee joint with a cylindrical coupling bolt and a spherical slide bush.
Figure 2D:
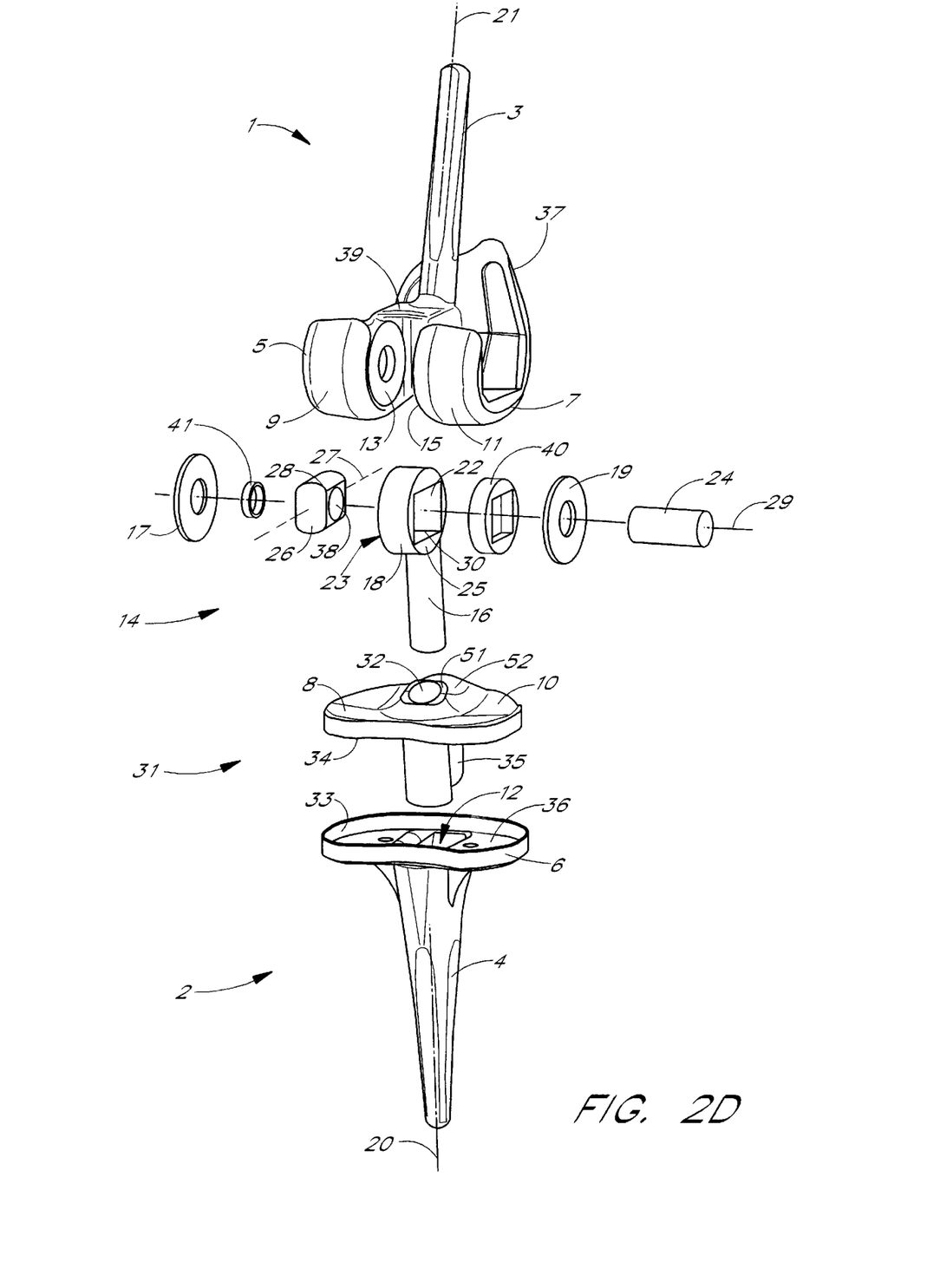
FIG. 2D is an exploded view of an endoprosthetic knee joint with a cylindrical coupling bolt and a cylindrical slide bush.

As shown in FIGS. 2C and 2D, corresponding to the third and fourth embodiments of the present invention, respectively, joint head 18 is mounted by means of a coupling bolt 24 to pivot about a substantially horizontal joint axis 29 in the side walls 13, 15 of the condyle shells 5, 7. The bore 22 in joint head 18 has a sliding surface 30, which is so shaped that it forms a bearing seat for a slide bush 26, which in the assembled state of the endoprosthetic knee joint is located between the coupling bolt 24 and the joint head 18, i.e., is thrust with its bore 38 on to the coupling bolt 24. In the embodiment shown in FIG. 2C, the slide bush has a spherical external peripheral surface 28, which co-operates with the correspondingly-shaped slide surface 30 of the joint head 18, and enables sub-division of the joint surfaces on the cylindrical coupling bolt 24 and the spherical slide bush 26: the cylindrical coupling bolt 24 takes over exclusively the flexion/extension movement between the coupling bolt and the slide bush, while the spherical slide bush 26 takes over both the varus/valgus movement and a rotational movement between slide bush and joint head. In order to reduce wear between the lateral surfaces 23, 25 of the joint head on the one hand and the lateral walls 13, 15, rotating against them, of the condyle shells 5, 7 on the other hand, discs 17, 19 are provided which are likewise thrust on to the coupling bolt 24.

FIGS. 3A, 3B, 3C and 3D show vertical sections through the femur portion 1 with mounted coupling portion 14, particularly showing the four different embodiments of the central medial portion of the coupling bolt 24 located within the bore 22 of the joint head 18. In the first and second embodiments as shown in FIGS. 2A and 2B, respectively, the medial portion has a spherical shape, or a cylindrical shape vertical to the axis 29, and is surrounded by a correspondingly-shaped bearing bush 40, which is let into the bore 22 of the joint head 18 and consists of plastics. The coupling bolt 24 is preferably non-rotarily mounted on the adjacent side walls 13, 15 of the condyle shells, for example by screwing on pins 42 or other methods that would be well know to those skilled in the art.

Figure 3A:
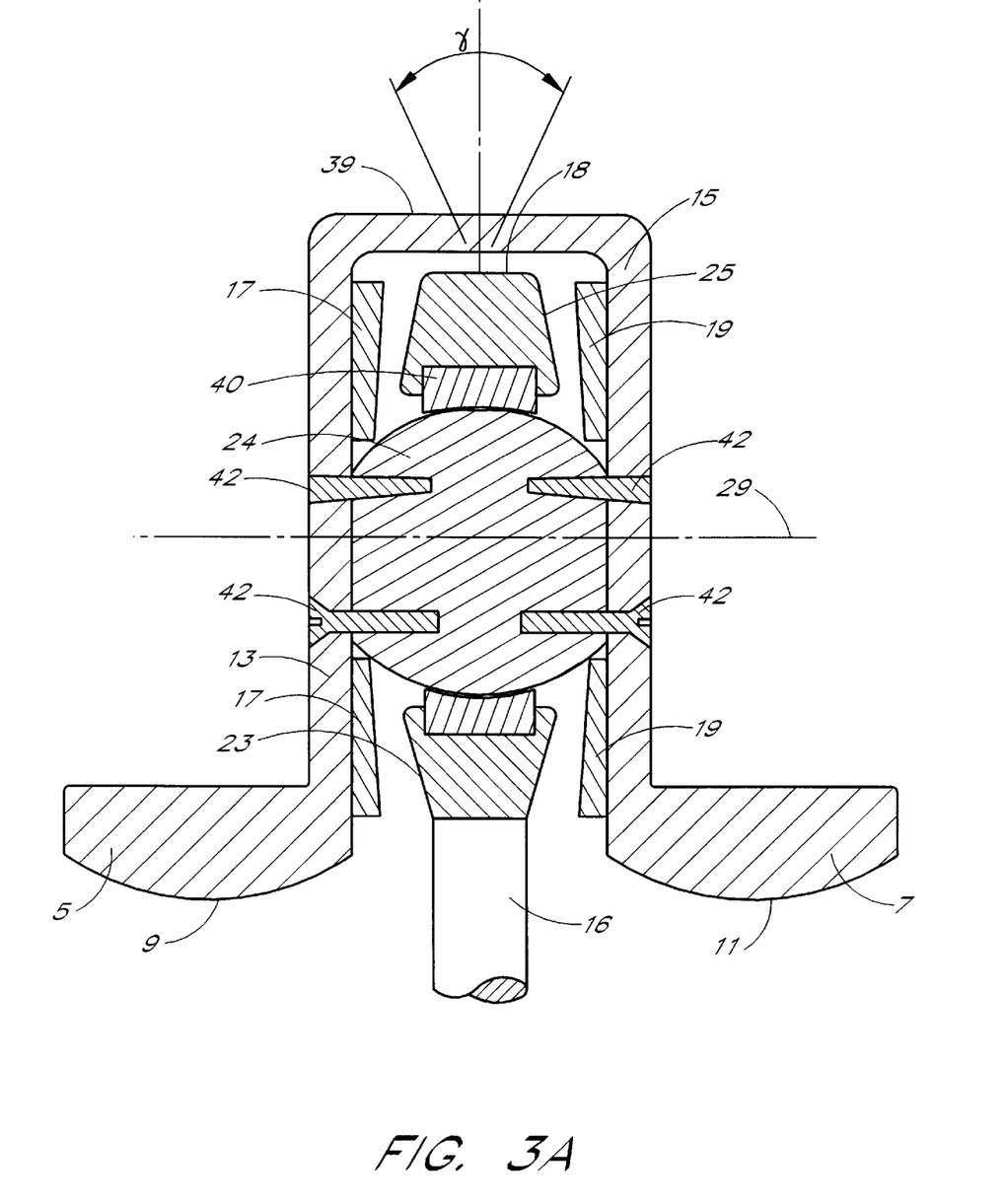
FIG. 3A is a sectional view of an endoprosthetic knee joint with a spherical coupling bolt.
Figure 3B:
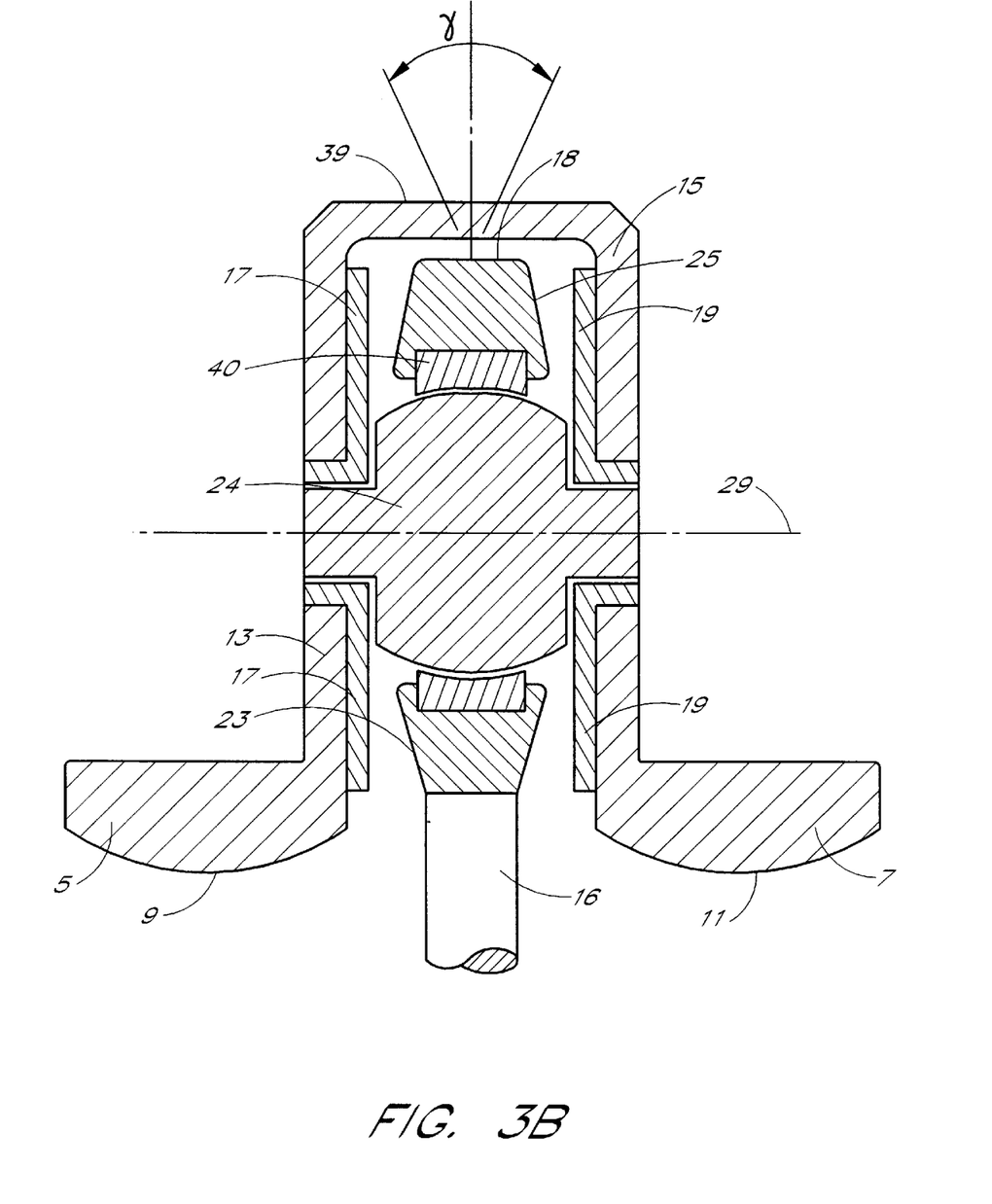
FIG. 3B is a sectional view of an endoprosthetic knee joint with a cylindrical coupling bolt.
Figure 3C:
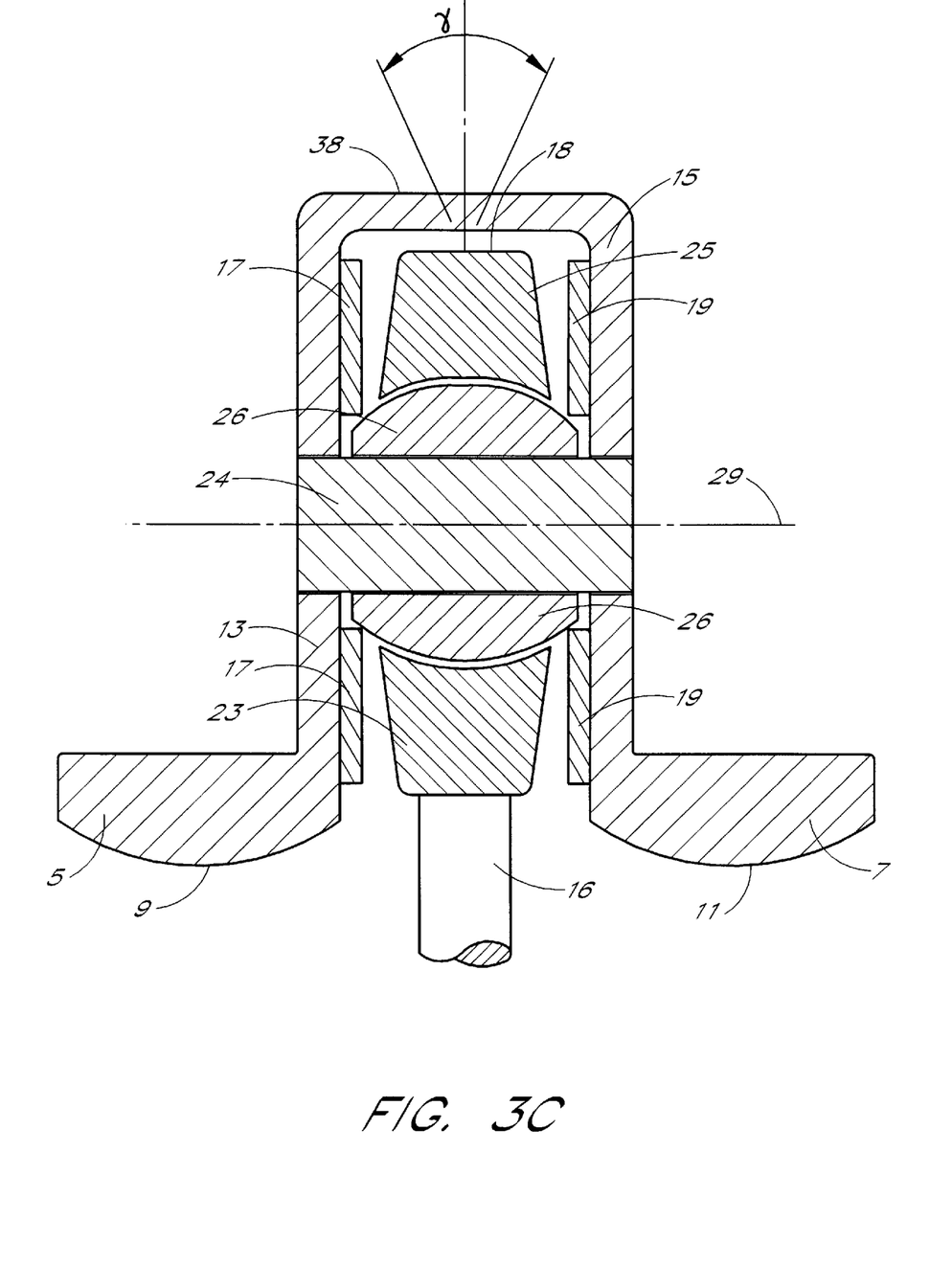
FIG. 3C is a sectional view of an endoprosthetic knee joint with a cylindrical coupling bolt and a spherical or cylindrical slide bush.
Figure 3D:
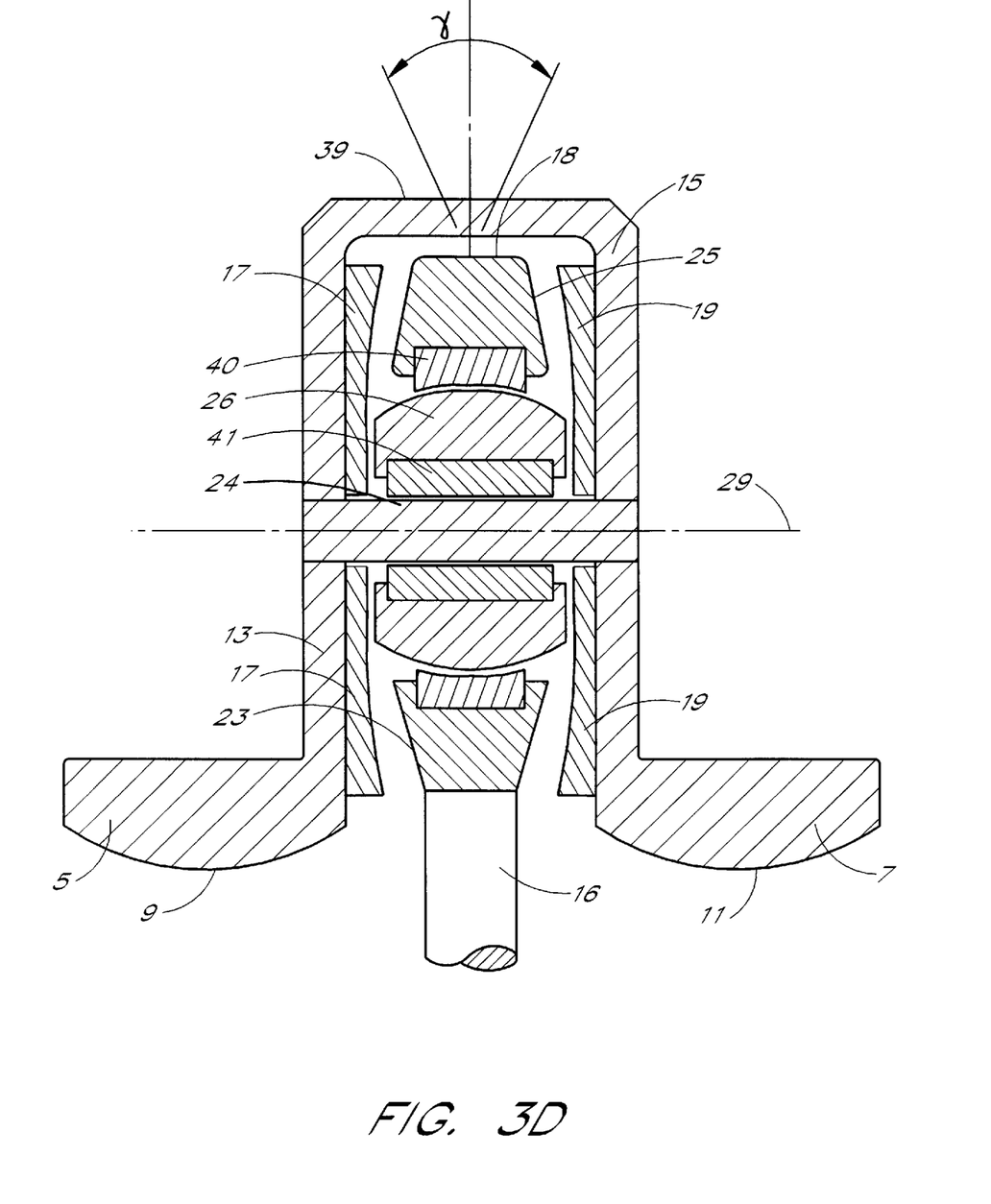
FIG. 3D is a sectional view of an endoprosthetic knee joint with a cylindrical coupling bolt and a spherical or cylindrical slide bush.

In the third and fourth embodiments, as shown in either of FIGS. 3C and 3D, the medial section of the coupling bolt 24 is designed in the form of a cylinder about its longitudinal axis 29 and is surrounded by a spherical slide bush 26, as in the third embodiment, or such a slide bush cylindrical and vertical to the axis 29, as in the fourth embodiment, which co-operates with a correspondingly-shaped sliding surface 30 of the joint head 18. The internal sliding surface of the slide bush 26 can also comprise plastics, which is let into the sliding bush in the form of a bearing bush 41, as shown in FIGS. 2D and 3D. The external peripheral surface of the slide bush would then consist of harder material, e.g., metal or ceramics. Alternatively, the slide bush can comprise a uniform material, more preferably plastics, metal or ceramics.

In each of the embodiments shown in FIGS. 3A, 3B, 3C and 3D, the side walls 13, 15 of the condyle shells 5, 7 are connected by an upper web to form a box 39, the parallel spacing of the side walls 13, 15 being such that the varus/valgus mobility is restricted to an angular range gamma of roughly ±10°. By means of corresponding conical formation of the side surfaces 23, 25 of the joint head 18, the joint head bears superficially on the discs 17, 19 during extreme varus/valgus deflection. In the lower region the side surfaces 23, 25 of the joint head 18 are again conically bevelled, in order to exclude unnecessary rotation of the joint head.

Figure 4:
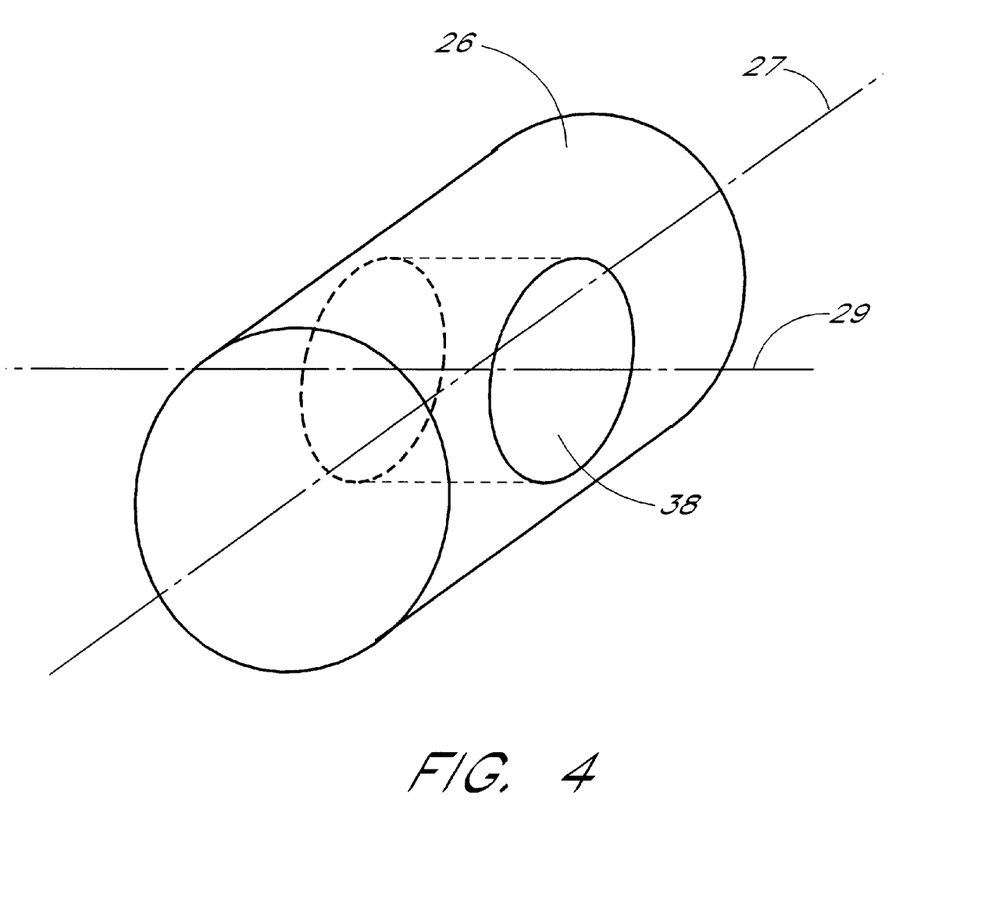
FIG. 4 is a perspective sketch of a cylindrical slide bush.

FIG. 4 shows a perspective sketch of a cylindrical slide bush 26 with a longitudinal axis 27 aligned ventrally-dorsally or anteriorly-posteriorly, and with a bore 38 for allowing passage to the coupling bolt 24. Naturally the coupling bolt 24 can have, in its central portion which is located in the assembled state of the endoprosthetic knee joint within the bore 22 of the joint head 18, a cylindrical shape as shown in FIG. 4 with the same alignment of the longitudinal axis 27. The cylindrical slide bush 26 or the cylindrical central portion of the coupling bolt 24 is accommodated in the correspondingly-shaped slide surface 30 of the joint head 18, which serves as a seat for the slide bush 26 or the central medial portion of the coupling bolt 24. In this embodiment also, with an indication of axial erroneous positions, varus-valgus compensation is possible in addition to the flexion/extension movement.

What is claimed is:

1. An endoprosthetic knee joint, comprising:
    a femur portion having at a lower end of a femur shaft convexly curved condyle shells with primary slide surfaces, said shells having two spaced-apart side walls forming an intercondylar space;
    a tibia portion having at an upper end of a tibia shaft a tibia plateau upon which there are formed secondary slide surfaces corresponding to the primary slide surfaces of the condyle shells, said tibia plateau having a recess extending axially in the tibia shaft; and
    a coupling portion having a coupling pin rotatably housed in said recess, an upper end of said coupling pin having a joint head projecting into said intercondylar space, said joint head having a bore extending transversely to the femur axis and pivotally mounted by a coupling bolt passing through the bore, said coupling bolt supported on the adjacent side walls of the condyle shells, a portion of the coupling bolt located within the bore of the joint head having a substantially spherically formed outer peripheral surface which co-operates with a correspondingly-shaped slide surface of the joint head.

2. An endoprosthetic knee joint according to claim 1, wherein a substantially parallel spacing of the side walls of condyle shells is so dimensioned that the varus/valgus mobility is restricted to a predeterminable angular range γ.

3. An endoprosthetic knee joint according to claim 1, further comprising respective discs located between the joint head and the side walls of the condyle shells.

4. An endoprosthetic knee joint, comprising:
    a femur portion having at a lower end of a femur shaft convexly curved condyle shells with primary slide surfaces, said shells having two spaced-apart side walls forming an intercondylar space;
    a tibia portion having at an upper end of a tibia shaft a tibia plateau upon which there are formed secondary slide surfaces corresponding to the primary slide surfaces of the condyle shells, said tibia plateau having a recess extending axially in the tibia shaft; and
    a coupling portion having a coupling pin rotatably housed in said recess, an upper end of said coupling pin having a joint head projecting into said intercondylar space, said joint head having a bore extending transversely to the femur axis and pivotally mounted by a coupling bolt passing through the bore, said coupling bolt supported on the adjacent side walls of the condyle shells, a portion of the coupling bolt located within the bore of the joint head having the shape of a cylinder whose axis extends transversely to the axis of the coupling bolt and which co-operates with a correspondingly-shaped slide surface of the joint head, the coupling bolt being pivotally mounted on the adjacent side walls of the condyle shells.

5. An endoprosthetic knee joint according to claim 4, wherein a substantially parallel spacing of the side walls of condyle shells is so dimensioned that the varus/valgus mobility is restricted to a predeterminable angular range γ.

6. An endoprosthetic knee joint according to claim 4, further comprising respective discs located between the joint head and the side walls of the condyle shells.

7. An endoprosthetic knee joint, comprising:

a femur portion having at a lower end of a femur shaft convexly curved condyle shells with primary slide surfaces, said shells having two spaced-apart side walls forming an intercondylar space;

a tibia portion having at an upper end of a tibia shaft a tibia plateau upon which there are formed secondary slide surfaces corresponding to the primary slide surfaces of the condyle shells, said tibia plateau having a recess extending axially in the tibia shaft; and a coupling portion having a coupling pin rotatably housed in said recess, an upper end of said coupling pin having a joint head projecting into said intercondylar space, said joint head having a bore extending transversely to the femur axis and pivotally mounted by a coupling bolt passing through the bore, said coupling bolt supported on the adjacent side walls of the condyle shells, a slide bush thrust on to the coupling bolt and located in the bore of the joint head, said slide bush enabling both a flexion/extension movement and a varus/valgus movement between the tibia portion and the femur portion.

8. An endoprosthetic knee joint according to claim 7, wherein the slide bush has a substantially spherically-shaped external peripheral surface with co-operates with a correspondingly-shaped slide surface of the joint head.

9. An endoprosthetic knee joint according to claim 8, wherein the slide bush is nonrotarily connected to the coupling bolt.

10. An endoprosthetic knee joint according to claim 7, wherein an external peripheral surface of the slide bush is made of a hard material such as metal or ceramic, while an internal slide surface of the slide bush is made of a soft material such as plastic and is in the form of a bearing bush.

11. An endoprosthetic knee joint according to claim 7, wherein the coupling bolt is non-rotarily mounted on the adjacent side walls of the condyle shells.

12. An endoprosthetic knee joint according to claim 7, wherein a substantially parallel spacing of the side walls of condyle shells is so dimensioned that the varus/valgus mobility is restricted to a predeterminable angular range γ.

13. An endoprosthetic knee joint according to claim 12, wherein the angular range lies between 0° and ±10°.

14. An endoprosthetic knee joint according to claim 7, further comprising respective discs located between the joint head and the side walls of the condyle shells.

15. An endoprosthetic knee joint according to claim 14, wherein the discs on inner sides facing the joint head are concavely conical in shape.

16. An endoprosthetic knee joint according to claim 7, wherein the side surfaces of the joint head are convexly conically formed in the radial direction on both sides.

17. An endoprosthetic knee joint according to claim 7, wherein the side surfaces of the joint head are proximally/distally bevelled in a roof shape and are flat anteriorly/posteriorly.

18. An endoprosthetic knee joint comprising:

a femur portion having at a lower end of a femur shaft convexly curved condyle shells with primary slide surfaces, said shells having two spaced-apart side walls forming an intercondylar space;

a tibia portion having at an upper end of a tibia shaft a tibia plateau upon which there are formed secondary slide surfaces corresponding to the primary slide surfaces of the condyle shells, said tibia plateau having a recess extending axially in the tibia shaft; and a coupling portion having a coupling pin rotatable housed in said recess, an upper end of said coupling pin having a joint head projecting into said intercondylar space, said joint head having a bore extending transversely to the femur axis and pivotally mounted by a coupling bolt passing through the bore, said coupling bolt supported on the adjacent side walls of the condyle shells, a slide bush thrust on to the coupling bolt and located in the bore of the joint head, said slide bush enabling both a flexion/extension movement and a varus/valgus movement between the tibia portion and the femur portion;

wherein the slide bush is in the shape of a cylinder whose axis extends transversely to the axis of the bore of the joint head, and which co-operates with a correspondingly-shaped slide surface of the joint head.

* * * * *